(12) United States Patent
McGrath et al.

(10) Patent No.: US 11,478,126 B2
(45) Date of Patent: Oct. 25, 2022

(54) VIDEO LARYNGOSCOPE AND VIDEO LARYNGOSCOPE INSERTION SECTION

(71) Applicant: Covidien AG, Neuhausen Am Rheinfall (GB)

(72) Inventors: Matthew John Ross McGrath, Edinburgh (GB); Peter Douglas Colin Inglis, Edinburgh (GB)

(73) Assignee: Covidien AG, Neuhausen Am Rheinfall (CH)

( * ) Notice: Subject to any disclaimer, the term of this patent is extended or adjusted under 35 U.S.C. 154(b) by 272 days.

(21) Appl. No.: 16/595,156

(22) Filed: Oct. 7, 2019

(65) Prior Publication Data

US 2020/0029793 A1 Jan. 30, 2020

Related U.S. Application Data

(62) Division of application No. 14/894,464, filed as application No. PCT/GB2014/051673 on May 30, 2014, now Pat. No. 10,448,804.

(30) Foreign Application Priority Data

May 30, 2013 (GB) .................... 1309714

(51) Int. Cl.
*A61B 1/267* (2006.01)
*A61B 1/00* (2006.01)
*A61B 1/04* (2006.01)

(52) U.S. Cl.
CPC ...... *A61B 1/00064* (2013.01); *A61B 1/00045* (2013.01); *A61B 1/00075* (2013.01); (Continued)

(58) Field of Classification Search
CPC combination set(s) only.
See application file for complete search history.

(56) References Cited

U.S. PATENT DOCUMENTS 5,584,795 A 12/1996 Valenti
6,251,069 B1 6/2001 Metzelopoulos et al.
(Continued)

FOREIGN PATENT DOCUMENTS

CN 101601574 A 12/2009
CN 103002792 A 3/2013
(Continued)

OTHER PUBLICATIONS

International Search Report for PCT/GB2014/051673, dated Nov. 13, 2014, 6 pages.
(Continued)

*Primary Examiner* — Sameh R Boles

(57) ABSTRACT

A video laryngoscope and elongate laryngoscope insertion section for a video laryngoscope, comprising a viewing port through which an imaging device within the insertion section can obtain images of a larynx, the insertion section extending between a distal end for insertion into a subject and an opposite proximal end, and having an inferior surface and an opposed superior surface, wherein the insertion section comprises a proximal region where the insertion section extends through a subject's teeth in use, a distal region extending to the distal end and an intermediate region therebetween, wherein the inferior surface of the insertion section comprises or consists of a curved region which extends from the proximal region through the intermediate region to the distal region, wherein the curved region of the inferior surface is continuously longitudinally curved along the length of the longitudinally curved region and wherein the longitudinal curvature of the curved region of the inferior surface varies in the intermediate region. Markings on an elongate laryngoscope insertion can be used to monitor depth of insertion and to indicate a path by which an endotracheal tube should be inserted.

19 Claims, 15 Drawing Sheets

(52) U.S. Cl.
CPC ...... *A61B 1/00096* (2013.01); *A61B 1/00142* (2013.01); *A61B 1/04* (2013.01); *A61B 1/267* (2013.01)

(56) References Cited

U.S. PATENT DOCUMENTS

| | | | |
|---|---|---|---|
| 6,378,523 | B1 | 4/2002 | Christopher |
| 6,494,828 | B1 | 12/2002 | Berall |
| 2005/0090712 | A1 | 4/2005 | Cubb |
| 2006/0020171 | A1 | 1/2006 | Gilreath |
| 2007/0167686 | A1 | 7/2007 | McGrath |
| 2007/0203396 | A1* | 8/2007 | McCutcheon ..... A61B 1/00082 600/173 |
| 2010/0256451 | A1 | 10/2010 | McGrath et al. |
| 2010/0312059 | A1* | 12/2010 | Mcgrath ........... A61M 16/0488 600/188 |
| 2012/0029292 | A1 | 2/2012 | Kae et al. |
| 2013/0060089 | A1 | 3/2013 | McGrath et al. |

FOREIGN PATENT DOCUMENTS

| | | |
|---|---|---|
| CN | 202776251 U | 3/2013 |
| GB | 2472926 A | 2/2011 |
| GB | 2481515 A | 12/2011 |
| WO | 2004096031 A1 | 11/2004 |
| WO | 2004096032 A1 | 11/2004 |
| WO | 2005089634 A1 | 9/2005 |
| WO | 2010091309 A1 | 8/2010 |
| WO | 2013072706 A1 | 5/2013 |

OTHER PUBLICATIONS

Written Opinion of the ISA for PCT/GB2014/051673, dated Nov. 13, 2014, 12 pages.
Chinese Office Action for Chinese Application No. 201480043136.9 dated Jan. 19, 2017, 9 pages.
GB Examination Report under Section 18(3); Application No. GB1309714.2, dated Mar. 31, 2017.
Extended European Search Report for EP Application No. GB1309714. 2, dated Aug. 1, 2017, 3 pages.
Extended European Search Report for EP Application No. 20201344.7 dated Jan. 19, 2021, 8 pages.

* cited by examiner

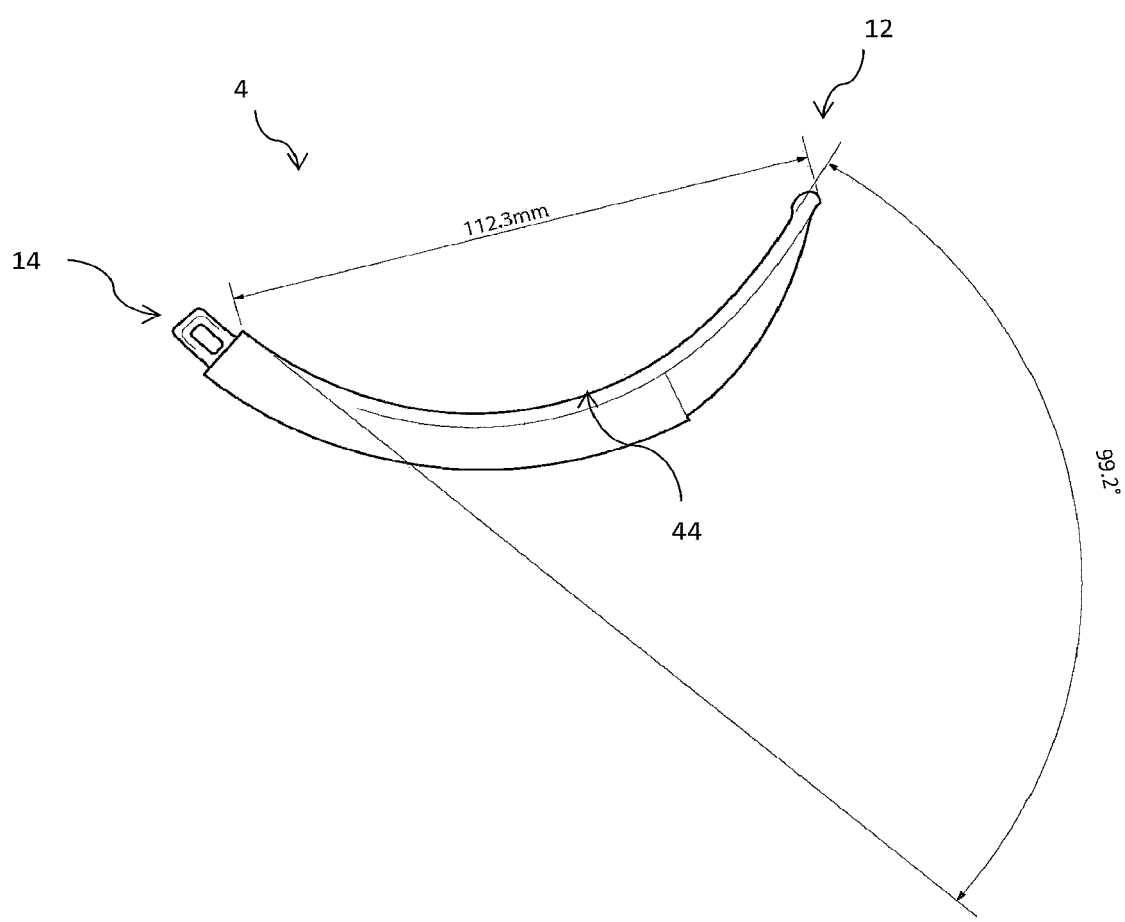

VIDEO LARYNGOSCOPE AND VIDEO LARYNGOSCOPE INSERTION SECTION

CROSS REFERENCE TO RELATED APPLICATION

This application is the Divisional of U.S. patent application Ser. No. 14/894,464 filed 27 Nov. 2015, which is the U.S. national phase of International Application No. PCT/GB2014/051673 filed 30 May 2014, which designated the U.S. and claims priority to GB Patent Application No. 1309714.2 filed 30 May 2013, the entire contents of each of which are hereby incorporated by reference.

FIELD OF THE INVENTION

The invention relates to the field of video laryngoscopes and insertion sections for video laryngoscopes.

BACKGROUND TO THE INVENTION

Laryngoscopes are medical devices in common use in oral and tracheal medical procedures, which may be used to obtain a view of the glottis or larynx, or to manipulate the tongue, glottis or larynx in order to facilitate insertion of endotracheal tubes or other instruments such as endoscopes, which may be separate pieces of equipment, or may be integral to a laryngoscope.

Laryngoscopes comprise insertion sections, which are the elongate part of a laryngoscope which extends into a subject's oral cavity during intubation. Insertion sections may be removably attachable to a laryngoscope body or integral parts of laryngoscopes or themselves function as laryngoscopes. As well as an insertion section, laryngoscopes typically comprises a handle which is usually elongate and which may be arranged at an angle to the proximal end of the insertion section or generally parallel to the proximal end of the insertion section, or at any angle therebetween. The insertion section and handle may be integrally formed.

Video laryngoscopes include an imaging device within the insertion section. The imaging device is typically a camera but may be a light transmission device (e.g. one or more fibre optic cables) extending to a camera which is not in the insertion section, for example, within a handle which remains outside of a subject's oral cavity in use. The imaging device may be part of the insertion section but it is also known for the imaging device to be part of the body of the laryngoscope, for example mounted to an insertion section retaining element which retains a demountable insertion section. An example of such as a device is shown in EP 1638451 (McGrath). Such devices are advantageous in that the demountable insertion section can be disposable and can protect the imaging device from contamination by bodily fluids, enabling the imaging device to be reused. The insertion section retaining element can also be a strengthening element, providing mechanical strength to the insertion section. Video laryngoscopes may have an integral screen or transmit images to a remote display through a wired or wireless interface.

Prior to the development of video laryngoscopes, intubation was typically carried out using direct laryngoscopy. In direct laryngoscopy, the intubater seeks to obtain a direct line of sight view of a subject's larynx. Some known insertion sections for laryngoscopes are substantially straight, such as Miller or Wisconsin blades. However, the blade of an insertion section is more commonly curved to better enter through a subject's oropharynx towards their larynx. For example, the most common curvature of an insertion section is what is commonly called the Macintosh curve. The curvature is relatively gentle and when inserted into a subject's oral cavity, the gently curved blade is used to lift and manipulate the tissue of the oral cavity, such as the tongue, out of the line of sight to allow an intubater a direct view of the subject's larynx.

However, video laryngoscopes enable a view of a subject's larynx to be obtained from an imaging device within the insertion section and therefore within a subject's oral cavity in use, without having to significantly lift or manipulate the tongue. This enables an indirect view of the larynx to be obtained. Some video laryngoscope insertion sections have sufficiently shallow curvature to enable a direct view to be obtained. In such cases, the ability to obtain a view of the larynx prior to intubation is of assistance but is not essential.

However, where there are anomalies within the oral cavity of the subject, or where an effective view of the larynx cannot be achieved with a direct view blade such as in instances where the subject's head and neck are not able to be moved to attain a direct line of sight of the larynx, it is often necessary to use an insertion section with a greater curvature to allow the blade to be inserted into the oral cavity. In this case, the intubater visualises the larynx indirectly using the video laryngoscope camera and screen. Insertion sections for use where a user cannot normally obtain a direct line of sight view of the larynx are referred to herein as indirect view insertion sections.

Some aspects of the invention address the technical problem of providing an insertion section of suitable shape to facilitate intubation by video laryngoscopy, particularly in relation to intubation of difficult airways. It is not uncommon for users, especially inexperienced users of video laryngoscopes, to concentrate on obtaining the best possible view from the camera of a video laryngoscope before starting to insert an endotracheal tube. In doing so, they typically insert the tip of the insertion section too far into the subject's oral cavity, elevating the epiglottis directly. This can often result in a lack of sufficient room to pass the endotracheal tube into the trachea as the tip of the insertion section is too anterior in the subject's mouth in contrast to when the tip of the insertion section is placed correctly fully into the vallecular to raise the epiglottis. This can cause a user to apply unnecessary force to try to make more room to pass the tube, or to position the tube more anteriorly. Incorrect positioning of the blade in the valecular can result in what is known as a "floppy epiglottis" (a misnomer used by users when epiglottis is lying in the line of sight of the vocal cords), usually caused by an insertion section not elevating the epiglottis appropriately to raise it out of the line of sight.

It is known to provide a substantially J-shaped insertion section, with a straight proximal region, a straight distal region and a defined bend or elbow therebetween. Likewise it is known to provide insertion sections with blades with a mixture of curved and straight sections with acute changes in angle or curvature between those sections (such as McGrath Series 5, Glidescope and Belscope) Such insertion sections may provide a reasonable view of the larynx but are difficult to insert. Some aspects of the invention seek to improve the shape of an insertion section to facilitate insertion into a subject, while enabling a good view of the larynx to be obtained. It is preferable to minimise distortion of tissue, avoid the use of excessive force and to avoid excessive friction with the subject anatomy.

Some aspects address the shape of the inferior surface of the insertion section as this surface contacts the patient's tongue during insertion. Some aspects address the shape of the insertion section as a whole, to facilitate intubation.

Some aspects of the invention seek to address the problem of users inserting an insertion section too far into a subject's mouth, or insufficiently far. It has been proposed to provide a single marking on the superior surface of a laryngoscope insertion section, indicative of a dividing line between typical depth of insertion for an adult and typical depth of insertion for a child. However, this is not satisfactory as there is a significant variation in the correct depth of insertion of an insertion section between subjects within each group, and so a single indicator line is not of practical assistance.

Some embodiments of the invention address technical problems arising from friction between an insertion section and a subject's tissues. Friction between an insertion section and tissues can cause trauma and affect the safety of an intubation. For example, the subject's lips may stick to the insertion section and become dragged over the lower incisors causing trauma and bleeding.

When intubating a subject using an indirect view laryngoscope, such as a video laryngoscope, users who were trained with traditional direct view Macintosh laryngoscopes may insert an endotracheal tube along the wrong path. During traditional direct view laryngoscopy, an endotracheal tube is run across the superior surface of the oral cavity. However, it is more appropriate to run an endotracheal tube close to the insertion section itself during indirect laryngoscopy. In insertion sections that have a steeper curve, it is most appropriate that the endotracheal tube runs close to the apex of the curve of the intermediate region of the insertion section that traverses the oral cavity. Some aspects of the invention address the problem of users inserting an endotracheal tube along a path which was appropriate for traditional Macintosh laryngoscopes, but which is not appropriate with a video laryngoscope, and more particularly an insertion section with a steep curve.

SUMMARY OF THE INVENTION

Within this specification and the appended claims, the inferior surface is the surface of an insertion section which faces the subject's tongue in use. The opposite surface is referred to as the superior surface. Words such as inferior, inferiorly, superior and superiorly are used in corresponding senses. A superior-inferior axis is a virtual axis extending parallel to the superior and inferior directions.

The words distal and distally refer to being towards the end of the insertion section which extends towards a subject's trachea in use and the words proximal and proximally refer to being towards the person carrying out intubation in use.

According to a first aspect of the invention there is provided an elongate laryngoscope insertion section comprising a viewing port through which an imaging device within the insertion section can obtain images of a larynx, the insertion section extending between a distal end for insertion into a subject and an opposite proximal end, and having an inferior surface and an opposed superior surface, wherein the insertion section comprises a proximal region where the insertion section extends through a subject's teeth in use, a distal region extending to the distal end and an intermediate region therebetween, wherein the inferior surface of the insertion section comprises or consists of a curved region which extends from the proximal region through the intermediate region to the distal region, wherein the curved region of the inferior surface (the curved region) is continuously longitudinally curved along the length of the longitudinally curved region and wherein the longitudinal curvature of the curved region of the inferior surface varies in the intermediate region.

The invention also extends in a second aspect to a video laryngoscope comprising an elongate laryngoscope insertion section according to the first aspect of the invention and an imaging device within the insertion section. The imaging device is configured to view images through the viewing port. The imaging device may be integral to the insertion section. The imaging device may comprise a cavity (such as a channel) for receiving an insertion section retaining member and/or an imaging device. The imaging device is typically adjacent to or integral with the viewing port.

The viewing port is typically a window through which an imaging device within the insertion section can view the larynx during use. The window may be integral to the imaging device, for example, the imaging device may be a camera comprising an imaging sensor and a lens and the window may be the lens of the camera. The window may not be flat, for example, it may comprise a prism to redirect light or other optical features.

The curved region typically extends along at least 80% or at least 90% of the length of the insertion section. Typically the curved region extends along all of the length of the insertion section which would extend into the mouth of a subject during normal operation, except optionally for the distal tip which may have another feature, such as a bobble to facilitate sliding across tissues.

The curved region may extend to the proximal end of the inferior surface of the insertion section. The curved region may extend to the distal end of the inferior surface of the insertion section. The viewing port may be in the intermediate region of the insertion section. However, in some embodiments, the distal region may extend from the viewing port to the distal tip of the insertion section.

The curved region typically extends to the distal end of the inferior surface of the insertion section or to a bobble at the distal end of the inferior surface of the insertion section.

It may be that the curved region of the inferior surface has a minima of longitudinal radius of curvature (maximum of longitudinal curvature) in the intermediate region of the insertion section.

It may be that the longitudinal radius of curvature of the curved region at the minima of longitudinal radius of curvature in the intermediate region of the insertion section is less than at any point of the curved region in the proximal and distal regions (and so the longitudinal curvature at the maximum of longitudinal curvature is greater than at any point of the curved region in the proximal and distal regions).

It may be that the longitudinal radius of curvature of the inferior surface varies continuously in the intermediate region.

Preferably, the inferior surface of the insertion section curves by more than 90°, and typically more than 96°, more than 98° or more than 99° from the proximal end of the insertion section to the distal end of the insertion section.

It may be that the longitudinal radius of curvature of the inferior surface in the intermediate region is not less than 75% (or not less than 85% or not less than 90%) of the minimum radius of curvature of the inferior surface in the proximal curved region.

By avoiding excessive longitudinal curvature in the intermediate region, the insertion section is easy to introduce into a subject. This contrasts with insertion sections having a discrete corner, or elbow, in the inferior surface.

The insertion section can therefore be rolled into a patient without pushing the anatomy around.

It may be that the longitudinal radius of curvature of the curved region (and therefore curvature) is constant in the proximal region.

It may be that the longitudinal radius of curvature of the curved region (and therefore curvature) is constant in the distal region.

We have found that it is especially advantageous to use an insertion section having an inferior surface with a first constantly curved region having a constant longitudinal radius of curvature (in the proximal region of the insertion section) and a second constantly curved region having a constant longitudinal radius of curvature (in the distal region of the insertion section) with an intermediate region having a variable longitudinal radius of curvature (which is typically less than the longitudinal radius of curvature of the first or second constantly curved regions) therebetween. The resulting shape is easier to insert than an insertion section having an inferior surface which is straight along much of the length, requiring a more defined bend or elbow.

Typically, the longitudinal radius of curvature of the curved region of the inferior surface has a minima in the intermediate region and the longitudinal radius of curvature of the curved region of the inferior surface increases to at least 150% or 175%, or preferably at least 200% of the longitudinal radius of curvature of the curved region at the said minima of longitudinal radius of curvature. (The minima of longitudinal radius of curvature is a maxima of curvature).

It may be that the longitudinal radius of curvature of the curved region in the proximal region is less than the longitudinal radius of curvature surface of the curved region in the distal region.

The longitudinal radius of curvature is preferably less than four times, or less than three times, or less than double, or less than 150% of the straight line distance from the proximal end to the distal end of the inferior surface of the insertion section, throughout the curved section.

The curved region may curve longitudinally in the proximal region of the insertion section with a mean (or constant, where the longitudinal radius of curvature is constant) longitudinal radius of curvature of 50%±5%, or preferably 50%±2.5% of the straight line distance from the proximal end of the insertion section to the distal end of the insertion section.

The curved region may curve longitudinally in the distal region of the insertion section with a mean (or constant, where the longitudinal radius of curvature is constant) longitudinal radius of curvature which is equal to or greater than the straight line distance from the proximal end of the insertion section to the distal end of the insertion section.

It may be that the minimum longitudinal radius of curvature of the curved region in the intermediate region is greater than 75% (and preferably greater than 80%, greater than 85% or more preferably greater than 90%) of the minimum longitudinal radius of curvature of the curved region in the proximal region.

Where the curved region has a constant curvature in the proximal region, the minimum longitudinal radius of curvature of the curved region in the proximal region will be the longitudinal radius of curvature of the curved region in the proximal region.

Accordingly, the maximum longitudinal curvature of the intermediate region of the insertion section is less (and so the minimum of longitudinal radius of curvature is greater) than in known laryngoscope insertion sections having a highly curved region or an elbow within the oropharynx in use.

The camera is situated in a similar location to insertion sections with acute changes in angle or curvature but without the awkward angle in the insertion section. This is achieved by an insertion section with a unique curving profile with a varying radius of curvature in the intermediate region which runs seamlessly into the constant radius of curvature of the proximal region. This shape, in conjunction with the slim line profile means that the curve of the intermediate portion sits lower in the oral cavity in use, and as such less force is required on the subject's tissues to place the tip of the blade in the vallecula and the camera therefore in the optimum position so as to gain a sufficient anterior view from the camera whilst also allowing sufficient room for the endotracheal tub to pass through the cords. This assists in overcoming known difficulty in placing the tube with a steeply curved blade.

Typically, the breadth of the insertion section is less than the depth of the insertion section at at least one part of the proximal region which is adjacent a subject's teeth in use.

By the breadth of the insertion section we refer to the lateral extent. By the thickness we refer to the displacement, parallel to a superior inferior axis, from the most inferior point on the inferior side of the insertion section to the most superior point on the superior side of the insertion section, through a given cross section orthogonal to the length of the insertion section.

The thickness of the insertion section may be constant in the intermediate region. The thickness of the insertion section may be constant in the proximal region. The thickness of the insertion section may be constant along the length of the insertion section at least from the proximal region to the viewing port. The thickness of the insertion section may be constant along the length of the elongate member.

The laryngoscope insertion section preferably comprises an inferior flange defining part of the inferior surface. The viewing port is typically located on a first lateral side of the insertion section and the inferior flange is typically located on the opposite lateral side of the insertion section. The inferior flange typically extends distally of the viewing port. The inferior flange may define the distal end of the insertion section. The inferior flange typically extends laterally of the elongate member (where present). It may be that the inferior flange extends laterally of the elongate member (where present) at least as far distally as the viewing port. It may be that the inferior flange extends laterally of the elongate member (where present) to the distal end of the elongate member. It may be that the inferior flange may extend laterally of the elongate member (wherein present) for less than 75%, or less than 60%, less than 50% or less than 40% of the distance along the inferior surface from the proximal end of the insertion section to the viewing port. The proximal end of the inferior flange may be tapered. This reduces the bulk of the inferior flange, facilitating tube insertion, while ensuring it extends laterally of the elongate member where required.

A support flange may extend laterally from the insertion section to resist flexion of the insertion section and thereby provide mechanical strength. The support flange typically extends from the insertion section in the opposite lateral direction to the inferior flange. The support flange typically extends from the insertion section from the same lateral side as the viewing port. Preferably the support flange extends along less than half, and preferably less than 40% or less than 30% of the length of the insertion section. Preferably, the support flange extends past the point of maximum longitudinal curvature of the curved region in the intermediate region of the insertion section. Preferably, the support flange extends past the viewing port (and typically the imaging device).

Accordingly, the support flange is provided for only a limited portion of the length of the insertion section, keeping down the bulk of the insertion section while providing mechanical strength.

It may be that the breadth of the insertion section is the same in the proximal region and the intermediate region.

It may be that the breadth of the insertion section in the intermediate section is greater than the breadth of the insertion section in the proximal region (for example, by 1-5% or by 1-10%).

The insertion section may comprise an elongate member which extends from the proximal end of the insertion section at least as far in a distal direction as the viewing port. A channel for receiving an insertion section retaining member of a laryngoscope body having an insertion section retaining member may extend from the proximal end of the elongate member. A flange may extend laterally from the inferior surface of the elongate member. The elongate member may have a constant breadth. The elongate member may be broader at the distal end of the elongate member than the proximal end of the elongate member. The breadth of the elongate member may increase from the proximal end of the elongate member to the distal end of the elongate member. The breadth of the elongate member may be 1-5% greater, or 1-10% greater adjacent the viewing port than at the proximal end of the elongate member.

This contrasts with known insertion section which are narrower at the viewing port than at the proximal end. Such devices function therefore have a generally wedge shaped profile and can be difficult to manoeuvre in the mouth.

As mentioned above, the invention also extends to a video laryngoscope comprising an elongate laryngoscope insertion section according to any one preceding claim and an imaging device within the insertion section.

Preferably, the viewing port is located superiorly of a point which is midway between the most inferior and most superior surfaces of the insertion section. Preferably, the imaging device is located superiorly of a point which is midway between the most inferior and most superior surfaces of the insertion section. Preferably, the imaging device is located superiorly of a point which is 60% of the way from the most inferior surface to the most superior surface of the insertion section.

The video laryngoscope may further comprise a display for displaying video images generated by the imaging device. The display may have a portrait orientation. That is to say, the images displayed on the display may have greater height (extent parallel to the inferior-superior axis) than width (lateral extent). The imaging device (which is typically a camera) will typically also have a portrait orientation, that is to say it will measure images with a greater angular spread in the inferior-superior axis than in a lateral direction.

The portrait orientation of the imaging device and display facilitates reliable intubation. This contrasts with known devices using a landscape or lateral orientation which have been found to contribute to 'tube blind spot' trauma risk with non-guided blades, due to the tube being loose and largely out of the visual field, potentially causing soft palette and similar trauma during insertion, and only appearing on the landscape display in the final moments before approaching the larynx. It can be preferable to provide an improved anterior view, while also providing an improved view of the soft palette, where blind spot related trauma can occur, to improve tube placement rather than to focus predominantly on lateral view.

It may be that the insertion section is an indirect view insertion section.

Typically, the maximum distance between the inferior surface of the insertion section and a straight line extending from the proximal end to the distal end of the inferior surface of the insertion section is greater than 22%, greater than 23%, greater than 24% or greater than 25% of the length of a straight line extending from the proximal end to the distal end of the inferior surface of the insertion section.

Typically, the inferior surface of the insertion section curves by more than 90° and typically more than 95°, more than 97° or more than 99° between the proximal and distal ends.

According to a third aspect of the invention there is provided an elongate laryngoscope insertion section extending between a distal end for insertion into a subject and a proximal end, and having an inferior surface and an opposed superior surface, wherein the superior surface is provided with a plurality of markings which are substantially equally longitudinally spaced.

Typically, the plurality of markings comprises at least three, or at least four markings. The plurality of markings typically form a scale. The plurality of markings may be increments of length from the distal end of the insertion section. The plurality of markings are typically increments of length from the distal end of the insertion section along the superior surface. Thus, they relate to the depth of insertion of the insertion section relative to the upper maxillary incisor teeth. In this case, the plurality of marking are equally longitudinally spaced along the inferior surface of the insertion section. However, the plurality of markings may be increments of straight line distance from the distal end of the insertion section. In this case, due to the curvature of the insertion section, although the plurality of markings are equally spaced from the distal end of the insertion section, there a small variation between spacing measured along the inferior surface of the insertion section.

The plurality of markings are located at the region of the insertion section which is adjacent a subject's upper (maxillary) teeth during intubation. The plurality of markings typically extend proximally and distally of a subject's upper (maxillary) teeth during intubation, at least for subjects at the middle of a range of sizes for which the insertion section is sized.

The markings may comprise or be adjacent to numbers indicative of length from the distal end of the insertion section (for example length along the superior surface or straight line distance).

Accordingly, a user may view the longitudinally spaced markings and establish the depth to which the insertion section has been introduced into a subject. Typically they do so after inserting the insertion section into a subject and before (and optionally during) insertion of an endotracheal tube into the subjects' trachea. This is advantageous at is can guide a user to the optimum depth of insertion of the insertion section into a subjects' oral cavity. The depth may also be recorded for training or monitoring purposes or can form part of the muscle memory training once optimal placement has been taught. The depth of insertion may be recorded and later retrieved to facilitate subsequent intubation of the same subject.

Still further, the plurality of equally longitudinally spaced markings can be referred to by a user to enable them to make an accurately judged change in the depth of insertion of the insertion section. They may decide to move the insertion section further into or out of the subject and use the plurality of markings to assess the distance by which the insertion section has moved. Thus, it is not essential for numbers indicative of length from the distal end of the insertion section to be provided.

The plurality of markings are also useful for communication during training of a user. A trainer may give verbal instructions, referring to the depth of insertion. The markings enable depth of insertion to be discussed during a procedure, enabling two people to work together. A user can look back and forwards repetitively between the markings on the superior surface of the insertion section and the display of the video laryngoscope during positioning of the video laryngoscope or subsequent intubation. They, or an assist, teacher or supervisor, can mark down the depth of insertion, or changes in depth of insertion, with reference to the plurality of markings.

The insertion section may comprise a depth monitor to monitor the depth to which the insertion section is inserted into a subject.

The invention extends to an elongate laryngoscope insertion section extending between a distal end for insertion into a subject and a proximal end, and having an inferior surface and an opposed superior surface, the insertion section comprising a depth monitor for monitoring the depth to which the insertion section is inserted into a subject.

The depth monitor may comprise a plurality of longitudinally spaced sensors for determining the extent to which the insertion section is located in the subject's mouth. The longitudinally spaced sensors may be longitudinally spaced along the superior surface of the insertion section. The longitudinally spaced sensors may be longitudinally spaced along the inferior surface of the insertion section.

The sensors may be optical sensors. They may detect whether they are in the patient's mouth from a decrease in the brightness of received light.

The invention extends to a video laryngoscope comprising the elongate insertion section, a display and a processor which controls the display, wherein the processor is configured (e.g. programmed) to cause the display to display information concerning the current or a previous depth of insertion (typically relating to the same subject). The laryngoscope may comprise a memory and the processor may store a measured depth of insertion in the memory. The processor may comprise an electronic interface for receiving depth of insertion data from or transmitting depth of insertion data to a remote patient data record database. The processor may be configured to cause the display to display an optimum or predetermined depth of insertion. The processor may be configured to cause the display to display an indicator as to whether the insertion section should be pushed further into, or retracted from, a subject's mouth.

The invention extends in a fourth aspect to a method of carrying out endotracheal intubation on a subject, the method comprising introducing a video laryngoscope comprising an elongate insertion section according to the third aspect of the invention into the subject, and then adjusting the depth to which the insertion section is inserted into the subject with reference to the plurality of markings on the superior surface.

The step of adjusting the depth to which the insertion section is inserted into the subject with reference to the plurality of markings may thereby guide a user as to the optimal placement of the insertion section. The step of adjusting the depth to which the insertion section is inserted into the subject with reference to the plurality of markings comprise guiding a user as to the distance by which they are adjusting the longitudinal position of the insertion section within a subject's mouth.

The method may then comprised inserting an endotracheal tube into the subject's trachea.

It may be that the depth of the insertion section is adjusted with reference to the plurality of markings after viewing the subject's trachea with the video laryngoscope and the method comprises the subsequent step of introducing an endotracheal tube into the subject's trachea.

The invention extends in a fifth aspect to an elongate laryngoscope insertion section extending between a distal end for insertion into a subject and a proximal end, and having an inferior surface and an opposed superior surface, wherein the inferior surface and/or the superior surface comprise a microscopically rough region.

The elongate laryngoscope insertion section may comprise a continuous body of clear plastic material which defines both a viewing port for an imaging device, having a smooth surface, and the or each microscopically rough region.

The microscopically rough regions will have a reduced contact surface area with a subject's tissues compared to a completely smooth surface, reducing the risk of damage to a subject's tissues during intubation. Typically, the microscopically rough regions appear frosted. This is due to light scattering by the microscopically rough regions. The smooth surface of the viewing port need not be flat and indeed typically comprises one or more surface features, such as a prism.

Accordingly, the continuous body of clear plastic material has both clear and frosted surface regions (where the surface is smooth and where the surface is microscopically rough respectively).

The invention extends in a sixth aspect to an elongate laryngoscope insertion section extending between a distal end for insertion into a subject and a proximal end, and having an inferior surface and an opposed superior surface, wherein the insertion section comprises an elongate member extending longitudinally along the insertion section and a lateral flange extending therefrom and having an inferior surface which forms at least some (or all) of the inferior surface of the laryngoscope insertion section, and an opposite superior surface, wherein the superior surface comprises a visual highlight.

The visual highlight indicates to a user the optimal path for an endotracheal tube to follow.

It may be that the insertion section comprises a viewing port through which an imaging device within the insertion section can obtain images of a larynx and the visual highlight extends along the superior surface of the flange distally of the viewing port.

The visual highlight may comprise an arrow pointing towards the distal end of the insertion section.

The visual highlight may also form part of a physically defined contact zone along which the endotracheal tube should run if placed in the optimal position so as to guide the intubater to position the endotracheal tube correctly. Such a contact zone may be added by injection moulding or mould labelling which may be in a different texture to the rest of the insertion section, which may include a region which does not have any microscopically rough regions.

The invention extends to a method comprising introducing a video laryngoscope comprising an insertion section according to the sixth aspect of the invention into a subject's oral cavity, obtaining a view of their larynx using the video laryngoscope, and then introducing an endotracheal tube adjacent to the visual highlight, or touching the visual highlight with the endotracheal tube.

The invention extends in a seventh aspect to an elongate laryngoscope insertion section extending between a distal end for insertion into a subject and a proximal end, and having an inferior surface and an opposed superior surface, wherein the insertion section comprises an elongate member extending longitudinally along the insertion section, the elongate member having a lateral wall and an elongate guide line extending longitudinally adjacent an optimal path for the insertion of an endotracheal tube into the trachea of a subject into which the insertion section has been introduced.

Accordingly, the guide line shows a user the path by which they should introduce an endotracheal tube into a subject's trachea. Although especially useful with an indirect view insertion section, particularly a more extremely curved insertion section, the feature may also be useful with an insertion section capable of a direct view any in any case helps to achieve the optimum placement of the endotracheal tube through the vocal cords under vision with the camera. The optimal path for an endotracheal tube would be the most direct route for the tube to pass requiring the least curvature whilst hugging the apex of the curve between the proximal and the intermediate regions ie similar to a racing line. The invention extends to a method comprising introducing a video laryngoscope comprising an insertion section according to the seventh aspect of the invention into a subject's oral cavity, obtaining a view of their larynx using the video laryngoscope, and then introducing an endotracheal tube adjacent the guide line, with reference to the guide line.

The invention extends in an eighth aspect to a video laryngoscope comprising a laryngoscope insertion section according to the first, third, fifth, sixth and/or seventh aspects of the invention. Optional features disclosed in relation to any one aspect of the invention are optional features of each aspect of the invention.

The invention also extends to a laryngoscope insertion section having a shape substantially as shown in FIGS. 3A to 3G and FIG. 5.

The invention also extends to a laryngoscope insertion section substantially as described herein and illustrated with reference to FIGS. 3A to 3G and FIG. 5.

The invention also extends to a laryngoscope insertion section having a shape and dimensions substantially as shown in FIGS. 6A to 6C.

The invention also extends to a video laryngoscope comprising a laryngoscope insertion section as claimed.

DESCRIPTION OF THE DRAWINGS

An example embodiment of the present invention will now be illustrated with reference to the following Figures in which:

FIGS. 6A, 6B and 6C are side, side and end views respectively of the insertion section shown in FIG. 5;

DETAILED DESCRIPTION OF AN EXAMPLE EMBODIMENT

Figure 1:
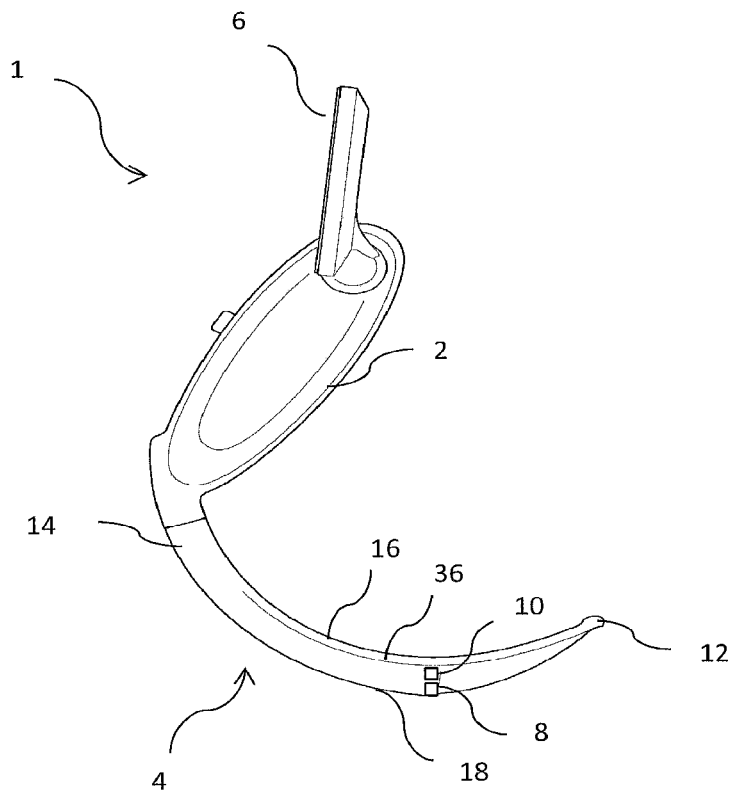
FIG. 1 is a side view of a video laryngoscope comprising an insertion section according to the present invention.

With reference to FIGS. 1 to 12, a video laryngoscope 1 comprises a handle 2 and an elongate insertion section 4 which extends from the handle. The handle has a display 6 for showing video images obtained by a camera 8, using light obtained from an LED light source 10. The camera is located in the superior half of the insertion section. The insertion section has a distal end 12 and an opposite proximal end 14. The insertion section has an inferior surface 16 which faces towards a subject's tongue in use and an opposite superior surface 18. An elongate member 34 extends along the insertion section longitudinally from the proximal end and a flange 36 extends laterally from and distally of the elongate member and, along with the inferior surface of the elongate member defines the inferior surface of the insertion section.

Figure 2:
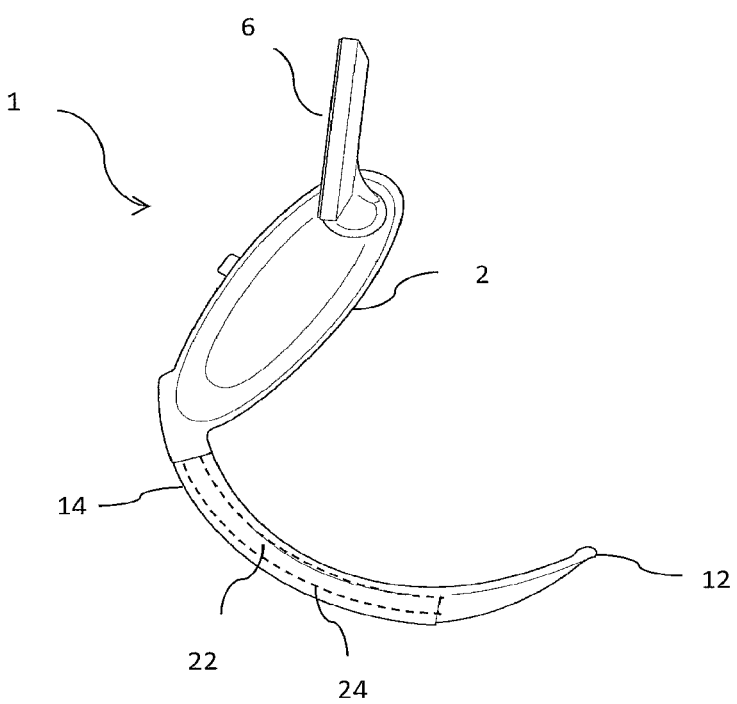
FIG. 2 is a corresponding side view showing a demountable insertion section, mounted on an insertion section retaining member.
Figure 3A:
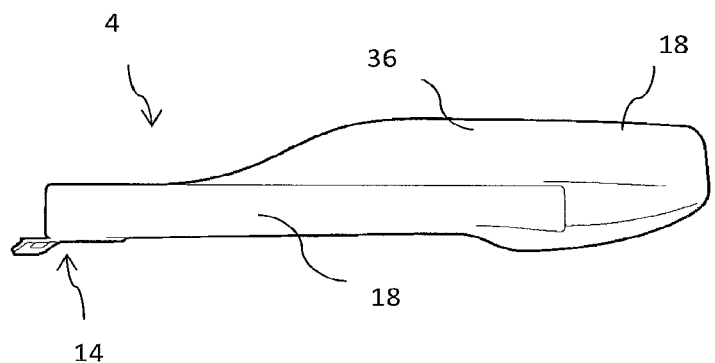
FIG. 3A is a bottom view of a laryngoscope insertion section.
Figure 3B:
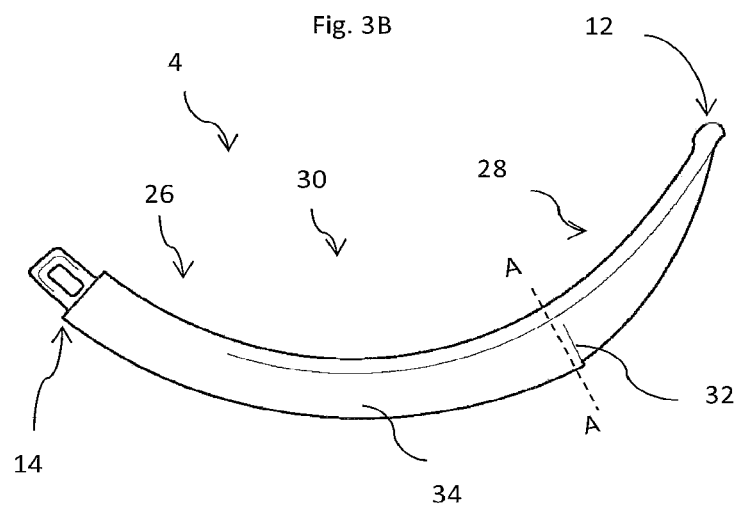
FIG. 3B is a side view of the laryngoscope insertion section.
Figure 3C:
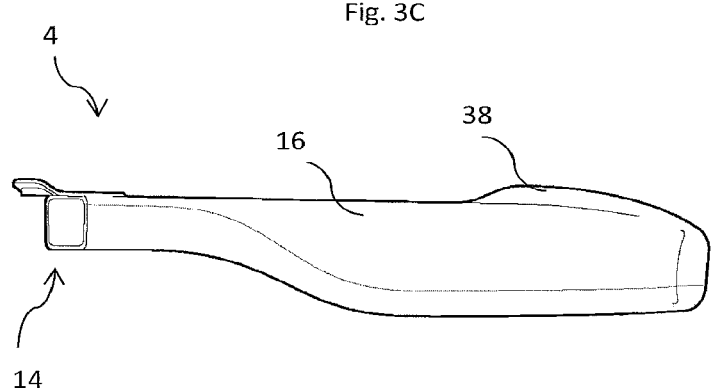
FIG. 3C is a plan view, from the inferior direction, of the insertion section.
Figure 3D:
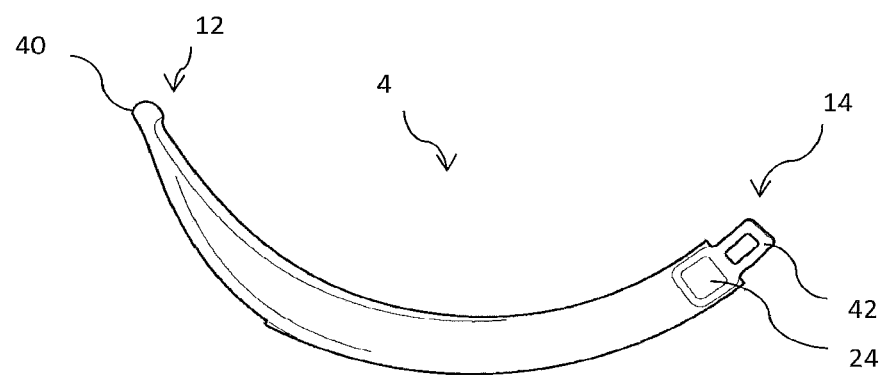
FIG. 3D is an opposite side view of the laryngoscope insertion section.
Figure 3E:
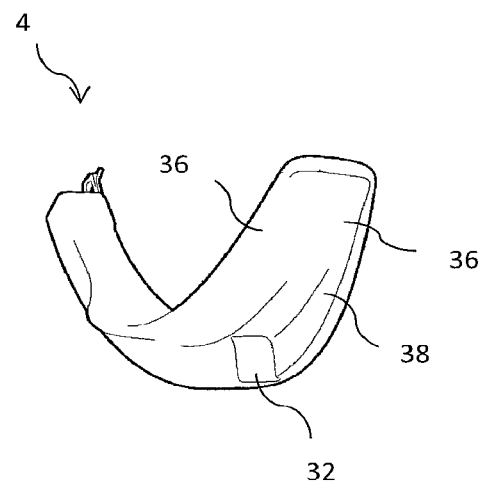
FIG. 3E is a perspective view from the distal end of the insertion section.
Figure 3F:
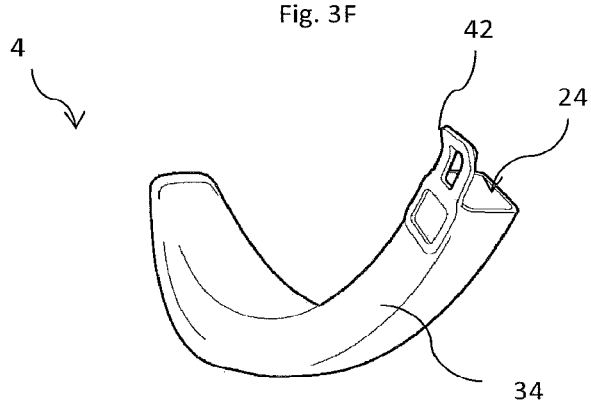
FIGS. 3F and 3G are perspective views of the insertion section.
Figure 3G:
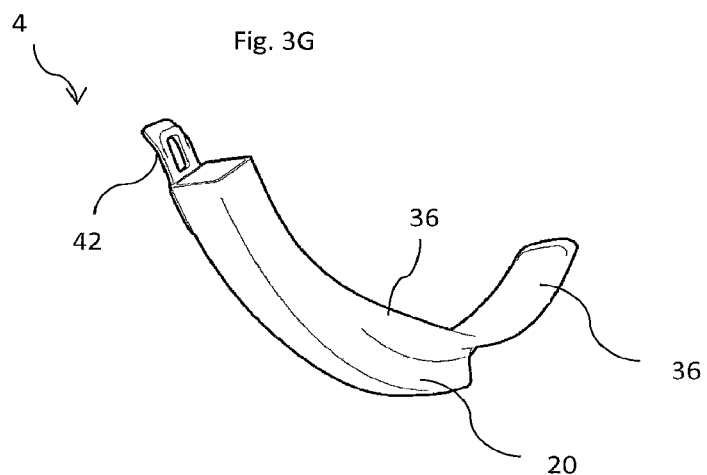
Figure 4:
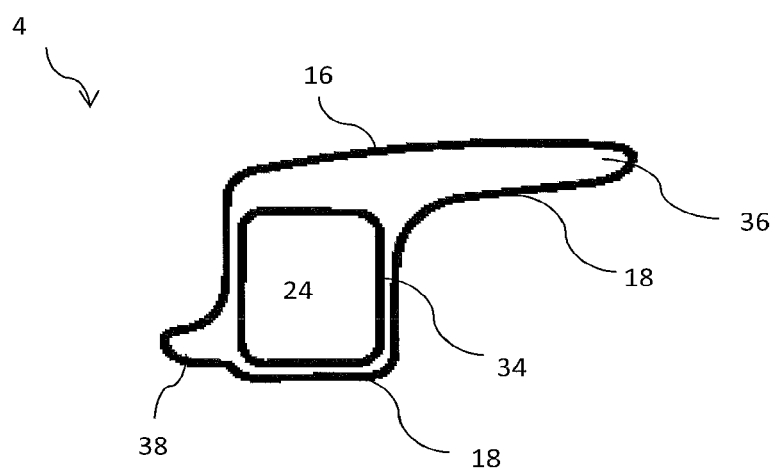
FIG. 4 illustrates the cross section of the insertion section through A-A.

With reference to FIG. 2, the handle has an elongate insertion section retaining member 22 extending therefrom, and the insertion section has an elongate channel 24 extending into the elongate member from the proximal end of the insertion section. The insertion section is formed from a transparent plastics material and includes a window 32, functioning as the viewing port, and having one or more prisms thereon to redirect light, to reduce light scattering and direct light from the required direction into the camera. The insertion section retaining member is formed from stainless steel and retains the camera 8 and light source 10, and the electrical wires (not shown) used to power the camera and light source and to receive images for display on the monitor. The elongate insertion section retaining member also functions as a strengthening element, resisting longitudinal bending and thereby providing mechanical support to the insertion section. Accordingly, the camera is in the insertion section but is not part of the insertion section. It is connected to the handle through the insertion section retaining member and collects images through the window.

However, in some embodiments, the handle is formed integrally with the insertion section. In some embodiments, the camera is part of the insertion section.

With reference to FIGS. 3A through 3G, the insertion section has a proximal region 26, where the insertion section extends between a subject's teeth in use, a distal region 28, which extends to the distal end, and an intermediate region 30 therebetween. A first flange 36, shown for example in FIGS. 3E and 4, extends laterally of the elongate member and distally of the viewing port and defines part of the inferior surface of the insertion section. A further flange 38 extends from a lateral wall 20 of the elongate member on the opposite lateral side from the first flange, near the superior surface of the elongate member, and provides additional mechanical support.

A bobble 40 is provided at the distal end of the insertion section, to help the tip of the insertion section glide across subject's tissues, and a clip 42, at the proximal end, retains the insertion section demountably by a laryngoscope handle in use.

Figure 5:
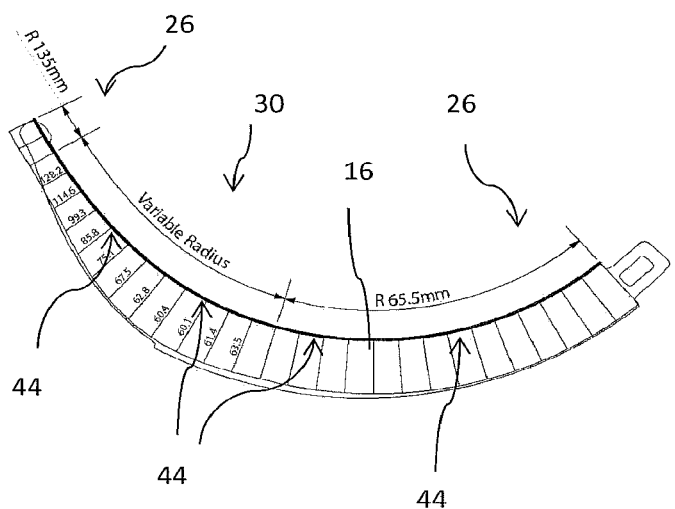
FIG. 5 illustrates the variation in radius of curvature of the inferior surface of an embodiment of the insertion section, with specified dimensions.

FIG. 5 illustrates the shape of the inferior surface of the insertion section. It can be seen that the inferior surface of the insertion section is continuously longitudinally curved at least from where it passes between the subject's teeth during use, to the bobble at the distal tip. This continuously curved section 44 functions as the curved portion. However, the curvature is not constant and numerical values of the longitudinal radius of curvature along the length of the insertion section are shown for a specific example embodiment. In the proximal region, there is a constant radius of curvature (65.5 mm in this example). Progressing distally along the insertion section, the curvature then increases in the intermediate region (and so the radius of curvature, which decreases when the curvature increases, drops to about 60 mm), and the curvature decreases again (and so the radius of curvature increases to about 135 mm), towards the distal end, such that the longitudinal curvature of the curved portion in the distal region is less than in the proximal region.

Accordingly, the longitudinal curvature is constant in the proximal region. There is a further (relatively short) constant curvature region near the distal tip, and a variable longitudinal curvature section intermediate the two constantly curved sections.

It has been found that this curvature profile means that, when the insertion section is positioned correctly, with the tip of the insertion section in the vallecular, the curve of the insertion section sits lower in the mouth in use than would be the case with a traditional Macintosh insertion section, and involves less tissue manipulation as a result, but still follows the anatomy of the subject. When the blade is correctly used, with the optimum depth of insertion into the subject's mouth, less force is required by the user of the laryngoscope to elevate the epiglottis than to gain a view of the vocal chords, than would otherwise be the case.

The flange 20 does not extend to the proximal end of the insertion section but is spaced apart from the proximal end by about 20% of the length of the insertion section portion. This makes the spatulate portion of the insertion section slim. This coupled with the sweeping steep curve and the constant height which is less than the width at the narrowest section of the insertion portion result in a blade which addresses the issue of optimising a sufficient anterior view from the camera whilst also allowing sufficient room for the endotracheal tube to pass through the cords.

Figure 6A:
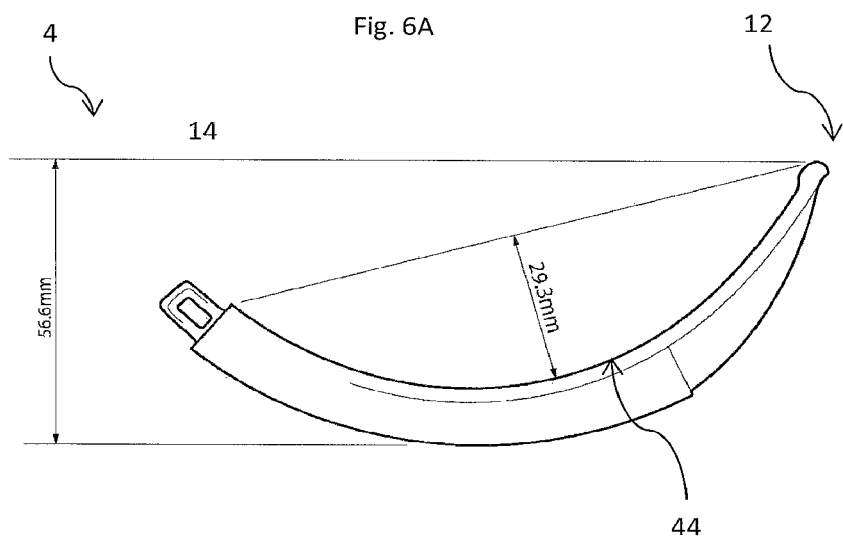
Figure 6C:
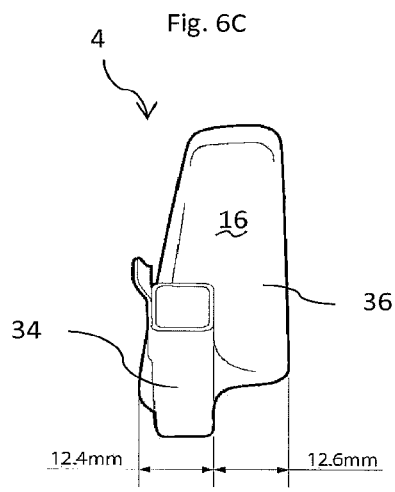

FIG. 5 and FIGS. 6A through 6C illustrate an example of an insertion section according to the present invention, with dimensions. The example which is shown is for use in subjects requiring Size 4 endotracheal tubes. The shape will vary for subjects of different sizes. This is an indirect view insertion section and it can be seen from FIG. 6B that the inferior surface of the insertion section curves by 99.2° between the proximal and distal ends. With reference to FIG. 6A the maximum distance between the inferior surface of the insertion section is 29.3 mm, which is 26.1% of the straight line distance between the proximal and distal ends of the inferior surface of the insertion section (112.3 mm, shown in FIG. 6C). These figures are indicative of a relatively highly curved insertion section, for obtaining an indirect view, suitable for use with difficult airways.

Figure 7A:
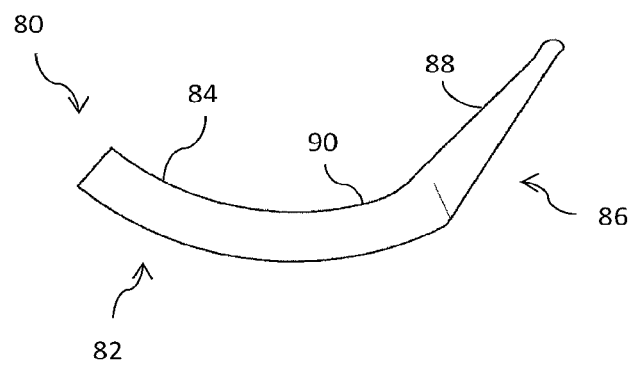
FIG. 7A is a side view of a known laryngoscope insertion section having a discrete bend in the inferior surface.

FIG. 7A is a view from a lateral direction of a known laryngoscope insertion section 80 (the dB5 disposable blade, available from Aircraft Medical Limited, Edinburgh, UK) which has a proximal region 82 with a constantly curved inferior surface 84, but a distal region 86 with a straight inferior surface 88 and a discrete bend 90 therebetween.

Figure 7B:
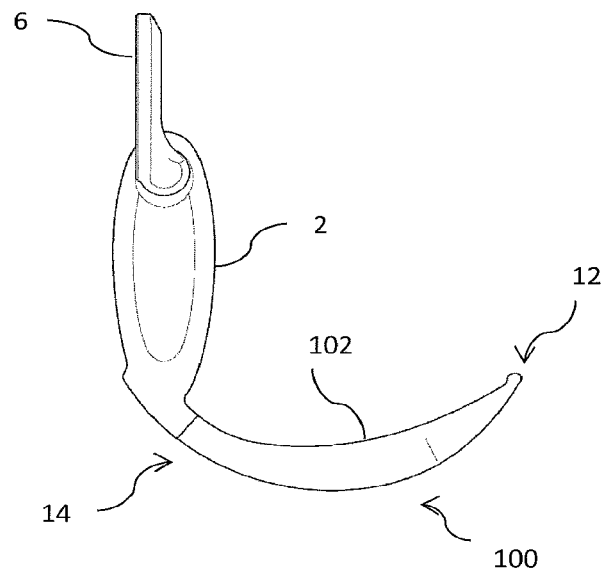
FIG. 7B is a side view of a known laryngoscope insertion having an inferior surface with a constant longitudinal curvature.

FIG. 7B is a view from a lateral direction of video laryngoscope with a known direct view laryngoscope insertion section 100 (shown in WO 2011/141751, Aircraft Medical) having an inferior surface 102 with a constant curvature 104.

Figure 7C:
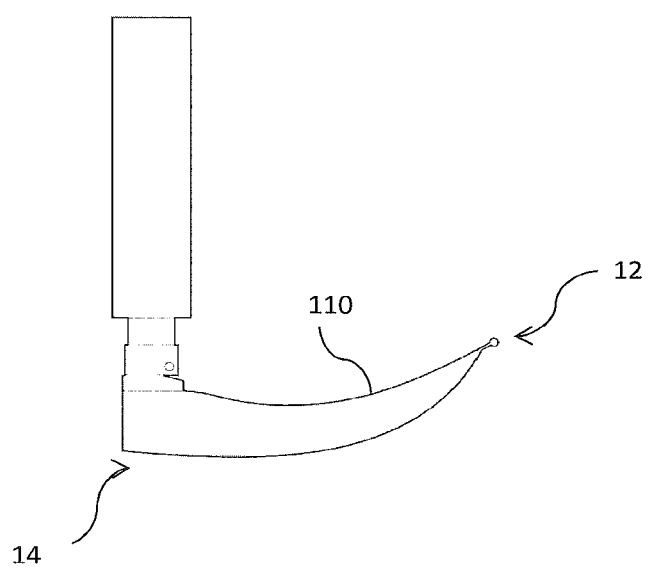
FIG. 7C is a side view of a standard laryngoscope with a Macintosh insertion section.

FIG. 7C is a view from a lateral direction of a widely-available traditional Macintosh laryngoscope, with a direct view insertion section 110.

Figure 7D:
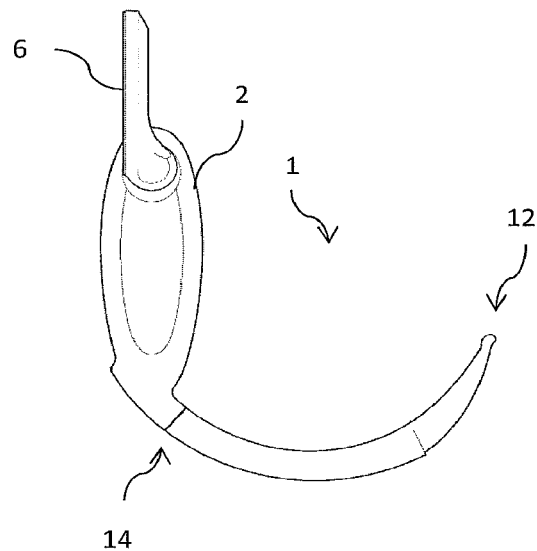
FIG. 7D is a side view of a laryngoscope with insertion section according to the present invention.

FIG. 7D is a view from a lateral direction of a laryngoscope insertion section according to the present invention.

Figure 7E:
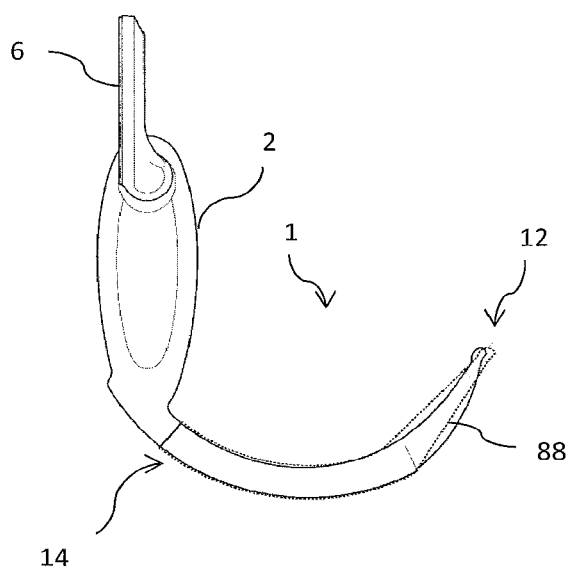
FIGS. 7E, 7F and 7G illustrated the laryngoscope of FIG. 7D with the insertion sections of FIGS. 7A, 7B and 7C respectively, overlaid as dashed lines.

FIG. 7E shows the insertion section of the present invention with the insertion section of FIG. 7A overlaid with a dashed line. It can be seen that the laryngoscope of the present invention is more curved, but the inferior surface does not have a discrete bend making the insertion section easier to insert.

Figure 7F:
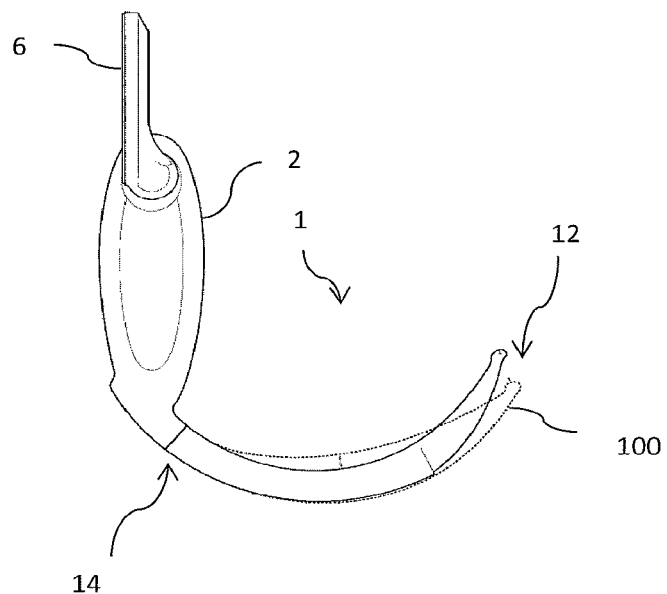

FIG. 7F shows the insertion section of the present invention with the insertion section of FIG. 7B overlaid with a dashed line. It can be seen that the laryngoscope of the present invention is more longitudinally curved, and has a variably longitudinal curvature, and provided a better indirect view of the trachea, while retaining the benefit of having a continuously longitudinally curved inferior surface, making it easy to insert without subject trauma.

Figure 7G:
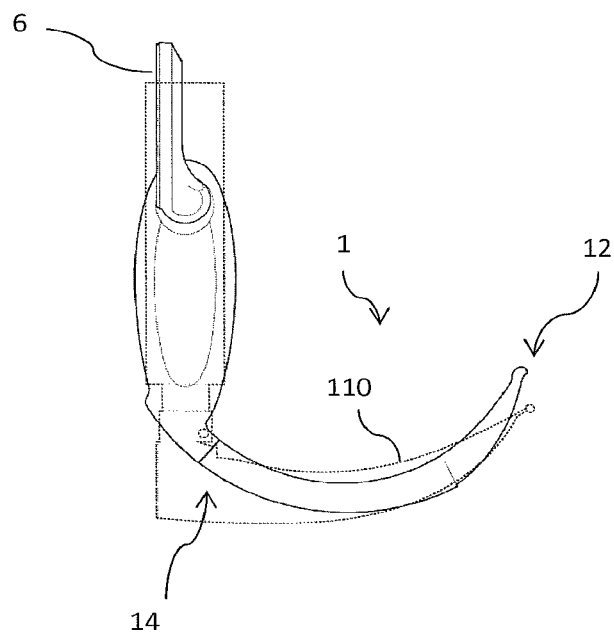

FIG. 7G shows the insertion section of the present invention with the traditional Macintosh insertion section of FIG. 7C overlaid with a dashed line. It can be seen that the laryngoscope of the present invention is more curved, providing a better angle to view the larynx indirectly during difficult airway intubations.

Figure 8:
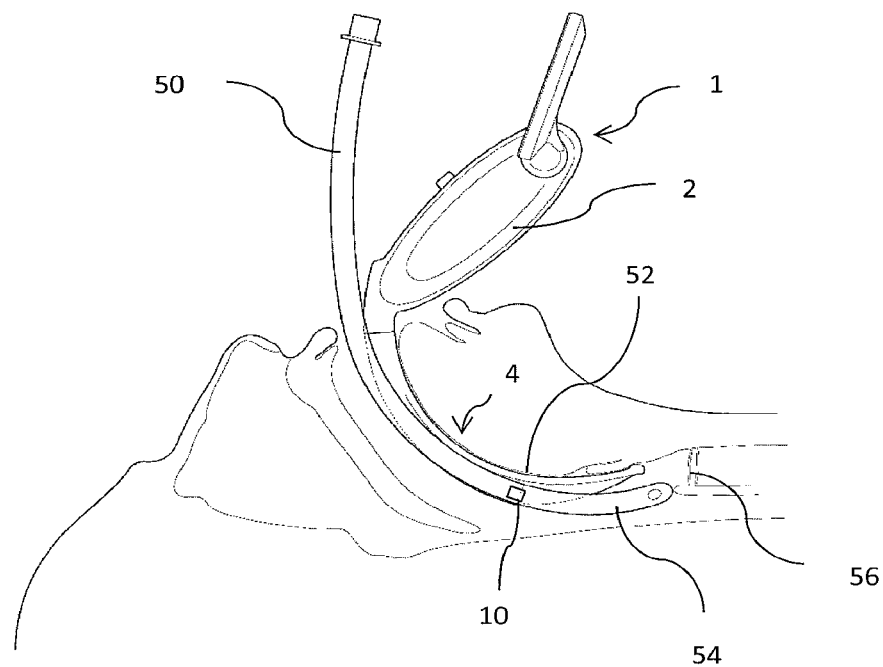
FIG. 8 illustrates incorrect endotracheal tube placement.
Figure 9:
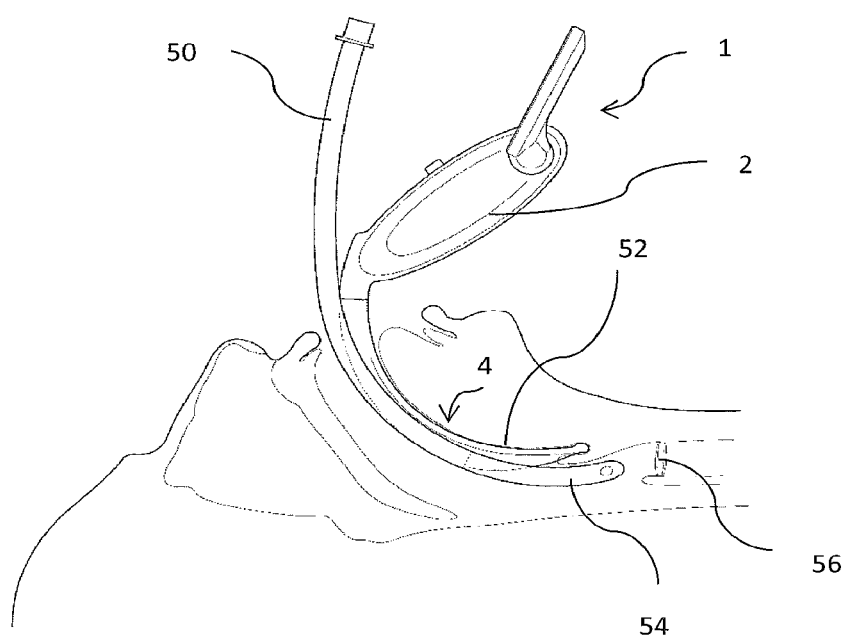
FIG. 9 illustrates correct placement of an endotracheal tube using the invention.

FIGS. 8 and 9 are cross-section through a subject undergoing tracheal intubation with a laryngoscope having an insertion section according to the invention. As the insertion section extends around the palette 52, a good view of the trachea 56 can be obtained from the camera. However, in FIG. 8, the insertion section has not been inserted correctly. The distal end of the insertion section restricts access of the endotracheal tube to the trachea. In FIG. 9, the insertion section has been inserted correctly. Users who are not familiar with video laryngoscopy may inadvertently make the error shown in FIG. 8 as the best view of the larynx is obtained when the insertion section has been inserted too far into the subject.

The shape of the insertion section, particularly the constantly curved inferior surface, with some greater, but not excessive, curvature in the intermediate region, has provided an insertion section which can be readily rolled into a patient, without the user having to push the patient's anatomy around. Without the curvature in the proximal region it is necessary to provide an excessively curved bend, which typically manifests itself in the camera region.

Figure 10A:
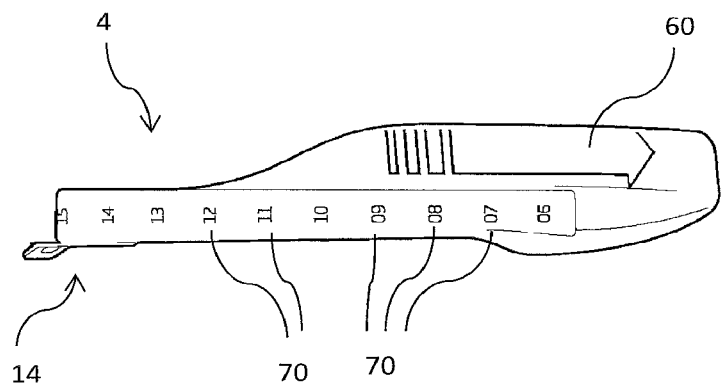
FIGS. 10A, 10B and 10C show the laryngoscope blade having various markings.
Figure 10B:
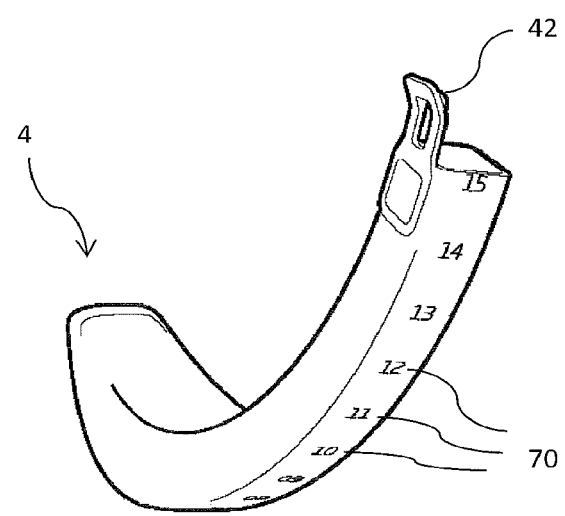

With reference to FIGS. 10A and 10B a longitudinal scale is provided on the superior surface of the insertion section, formed by a plurality of markings 70, which are equally longitudinally spaced. In this example, the markings are numbers, spaced apart by 1 cm, and each is a measure of the distance from the marking to the distal end of the insertion section, along the superior surface of the insertion section.

The markings enable a user to assess the depth of insertion of the insertion section, by reference to the position of the markings relative to the upper (maxillary) incisor teeth of the subject. This enables a user to determine the optimum depth of insertion, and the optimum technique for using a video laryngoscope with the insertion section.

The absolute value of depth of insertion may be recorded for a particular subject. The depth of insertion which is employed in a particular procedure may be stored, to provide a record of the procedure. The optimum depth of insertion may be looked up, for example, from a table of suitable depth of insertions for given sizes of the subject, or from measurements of the subject.

The markings can be used during intubation to avoid excessive insertion of the insertion section as shown in FIG. 8. The markings can also be used to make relative adjustments of depth of insertion, for example an optimum view can be obtained, and the user might then retract the insertion section by a predetermined distance, for example 1 cm, using the position of the markings relative to the subject's maxillary teeth, to judge the distance of movement.

Figure 10C:
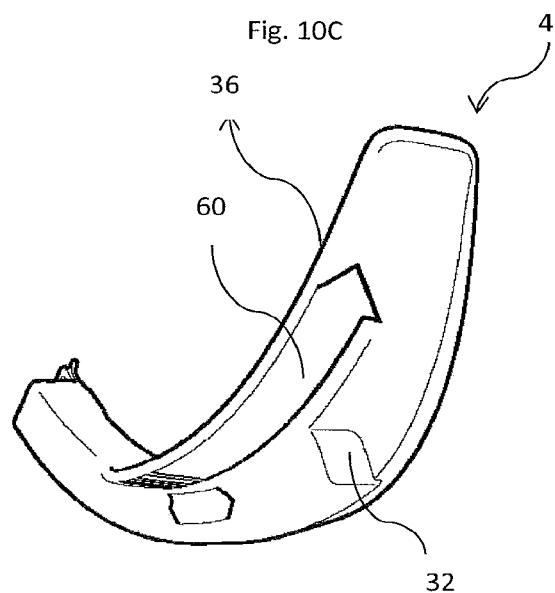
Figure 11:
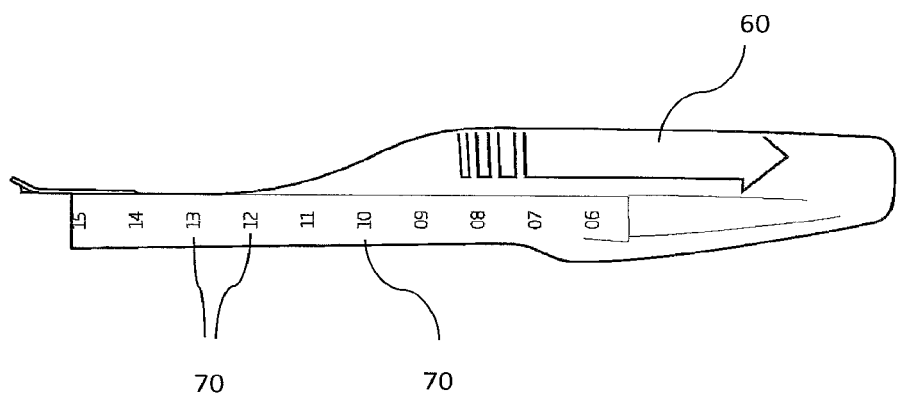
FIG. 11 shows the inferior surface of the insertion section, with markings, uncurled.

With reference to FIGS. 10A, 10C and 11, a visual highlight 60 is provided on the superior surface of the flange 36. The visual highlight serves to indicate to a user that they should insert the endotracheal tube along a path which is very close to, or touching the superior surface of the flange. The visual highlight may comprise one or more of an arrow pointing in a distal direction, a picture of an endotracheal tube and text. The visual highlight may indicate a contact zone which an endotracheal tube should contact during insertion. The visual highlight may be moulded. The visual highlight may be printed. The visual highlight may be etched. The visual highlight may be an embedded image, for example during moulding (e.g. using a twin shot mould).

Figure 12:
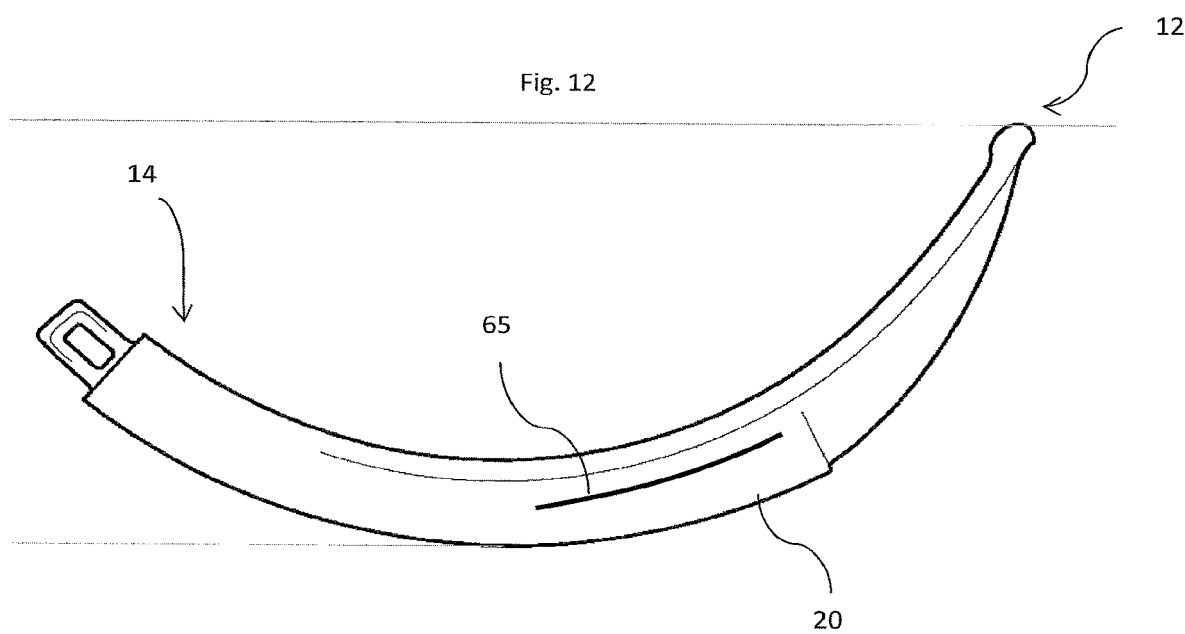
FIG. 12 is a lateral view of an insertion section.

With reference to FIG. 12, the lateral wall of the insertion section has an elongate guide line 65 extending longitudinally adjacent an optimal path for the insertion of an endotracheal tube into the trachea of a subject into which the insertion section has been introduced. The guide line, which might for example be a ridge or image, assists a user in introducing a tube along the optimum line.

The optimum line for introduction of an endotracheal tube generally hugs the longitudinal curve of the superior surface of the flange adjacent the viewing port. The optimum line for introduction may be the most direct route for an endotracheal tube, typically taking into account the built in curvature of an endotracheal tube. The optimum line may require least flexion of the endotracheal tube.

In some embodiments, the insertion section includes one or more microscopically rough surface regions located on the inferior and superior surfaces of the insertion section. Microscopically rough surface sections can be obtained by corresponding texturing of a mould used to form the insertion section, or by grinding, for example.

The microscopically rough surface sections present a lower contact area to skin than would be the case if the surfaces were completely smooth, reducing friction. This has the effect of a reducing the risk of damage to the lips, which might otherwise be dragged onto and cut by a subject's teeth during use.

The microscopically rough areas scatter light and so give the insertion section a frosted appearance. However, the microscopically rough surface regions do not extend across the viewing port, where they would block the camera. In these embodiments, an insertion section with microscopically rough surface regions on the inferior and superior surface, but not on the viewing port, can be made predominantly, and in some embodiments entirely, from a single moulded transparent plastics piece.

Further variations and modifications fall within the scope of the invention herein disclosed.

The invention claimed is:

1. An elongate laryngoscope insertion section comprising a viewing port through which an imaging device within the insertion section can obtain images of a larynx, the insertion section extending between a distal end for insertion into a subject and an opposite proximal end, and having an inferior surface and an opposed superior surface, wherein the insertion section comprises a proximal region where the insertion section extends through a subject's teeth in use, a distal region extending to the distal end and an intermediate region therebetween, wherein the inferior surface of the insertion section comprises a curved region which extends from the proximal region through the intermediate region to the distal region, wherein the curved region of the inferior surface is continuously longitudinally curved along the length of the longitudinally curved region and wherein the longitudinal curvature of the curved region of the inferior surface:

varies in the intermediate region; and is constant in at least one of the distal region or the proximal region.

2. An elongate laryngoscope insertion section according to claim 1, wherein the curved region of the inferior surface has a minima of longitudinal radius of curvature in the intermediate region of the insertion section.

3. An elongate laryngoscope insertion section according to claim 2, wherein the longitudinal radius of curvature at the minima of longitudinal radius of curvature of the curved region in the intermediate region of the insertion section is less than at any point of the curved region in the proximal and distal regions.

4. An elongate laryngoscope insertion section according to claim 2, wherein the longitudinal radius of curvature of the curved region of the inferior surface varies continuously in the intermediate region.

5. An elongate laryngoscope insertion section according to claim 2, wherein the longitudinal radius of curvature of the curved region of the inferior surface in the intermediate region is not less than 75% of the minimum radius of curvature of the inferior surface in the proximal curved region.

6. An elongate laryngoscope insertion section according to claim 2 wherein the longitudinal radius of curvature of the curved region of the inferior surface is constant in the proximal region.

7. An elongate laryngoscope insertion section according to claim 2, wherein the longitudinal radius of curvature of the curved region of the inferior surface is constant in the distal region.

8. An elongate laryngoscope insertion section according to claim 7, wherein the longitudinal radius of curvature of the curved region in the proximal region is less than the longitudinal radius of curvature surface of the curved region in the distal region.

9. An elongate laryngoscope insertion section according to claim 1, wherein the minimum longitudinal radius of curvature of the curved region in the intermediate region is greater than 80% of the minimum longitudinal radius of curvature of the curved region in the proximal region.

10. An elongate laryngoscope insertion section according to claim 1, wherein the insertion section is an indirect view insertion section.

11. An elongate laryngoscope insertion section according to claim 1, wherein the superior surface is provided with a plurality of markings which are substantially equally longitudinally spaced.

12. An elongate laryngoscope insertion section extending between a distal end for insertion into a subject and a proximal end, and having an inferior surface and an opposed superior surface,
   wherein the superior surface is provided with a plurality of markings which are variably spaced based on a curvature of the insertion section, and
   wherein the interior surface has a first portion with a constant radius of curvature and a second portion with a variable radius of curvature.

13. An elongate laryngoscope insertion section according to claim 12, wherein the plurality of markings are increments of length from the distal end of the insertion section along the superior surface.

14. An elongate laryngoscope insertion section according to claim 12, wherein the plurality of markings are in increments of straight line distance from the distal end of the insertion section.

15. An elongate laryngoscope insertion section according to claim 12, wherein the insertion section comprises a depth monitor to monitor the depth to which the insertion section is inserted into a subject.

16. An elongate laryngoscope insertion section according to claim 15, wherein the depth monitor comprises a plurality of longitudinally spaced sensors for determining the extent to which the insertion section is located in the subject's mouth.

17. An elongate laryngoscope insertion section according to claim 12, wherein an individual marking of the plurality of markings comprises a numerical indicator representative of a distance from the individual marker to the distal end.

18. An elongate laryngoscope insertion section according to claim 12, wherein the plurality of markings terminate proximally of a viewing port forming an end face of an elongate channel of the insertion section.

19. A laryngoscope comprising:
   a display screen;
   an imaging device; and
   an elongate laryngoscope insertion section comprising:
      a viewing port through which the imaging device can obtain images of a larynx, the insertion section extending between a distal end for insertion into a subject and an opposite proximal end;
      a proximal region where the insertion section extends through a subject's teeth in use;
      a distal region extending to the distal end;
      an intermediate region between the distal region and the proximal region,
      an inferior surface having a curved region that extends from the proximal region through the intermediate region to the distal region, wherein the inferior surface of the insertion section comprises a curved region which extends from the proximal region through the intermediate region to the distal region, wherein the curved region of the inferior surface is continuously longitudinally curved along the length of the longitudinally curved region and wherein the longitudinal curvature of the curved region of the inferior surface:
   varies in the intermediate region; and
   is constant in at least one of the distal region or the proximal region.

* * * * *